US012239503B2

(12) United States Patent
Chen et al.

(10) Patent No.: US 12,239,503 B2
(45) Date of Patent: Mar. 4, 2025

(54) MAGNETIC-FIELD-ADJUSTABLE MICROMAGNETIC ORTHODONTIC ACCELERATOR

(71) Applicant: Union Hospital, Tongji Medical College, Huazhong University of Science and Technology, Wuhan (CN)

(72) Inventors: LiLi Chen, Wuhan (CN); JiWei Sun, Wuhan (CN); QingMing Tang, Wuhan (CN); JunYuan Zhang, Wuhan (CN)

(73) Assignees: Union Hospital, Wuhan (CN); Tongji Medical College, Wuhan (CN); Huazhong University of Science and Technology, Wuhan (CN)

( * ) Notice: Subject to any disclaimer, the term of this patent is extended or adjusted under 35 U.S.C. 154(b) by 168 days.

(21) Appl. No.: 18/097,544

(22) Filed: Jan. 17, 2023

(65) Prior Publication Data

US 2024/0058098 A1    Feb. 22, 2024

Related U.S. Application Data

(63) Continuation of application No. PCT/CN2022/140300, filed on Dec. 20, 2022.

(30) Foreign Application Priority Data

Aug. 17, 2022   (CN) .......................... 202210986748.8

(51) Int. Cl.
*A61C 7/00* (2006.01)
*A61N 2/00* (2006.01)
*A61N 2/06* (2006.01)

(52) U.S. Cl.
CPC ................ *A61C 7/00* (2013.01); *A61N 2/002* (2013.01); *A61N 2/004* (2013.01); *A61N 2/06* (2013.01)

(58) Field of Classification Search
CPC .......... A61N 2/002; A61N 2/004; A61N 2/06; A61C 7/00; A61C 7/006
See application file for complete search history.

(56) References Cited

U.S. PATENT DOCUMENTS 4,484,895 A * 11/1984 Smiley ................... A61C 7/006
433/18
6,398,713 B1 * 6/2002 Ewing ...................... A61N 2/06
600/9

(Continued)

FOREIGN PATENT DOCUMENTS

| CN | 101175452 | 5/2008 |
|---|---|---|
| CN | 114795523 | 7/2022 |

(Continued)

OTHER PUBLICATIONS

International Search Report issued in PCT/CN2022/140300 on Apr. 30, 2023 and translation thereof.

*Primary Examiner* — Ralph A Lewis
(74) *Attorney, Agent, or Firm* — ARC IP Law, PC; Joseph J. Mayo (57) ABSTRACT

A magnetic-field-adjustable micromagnetic orthodontic accelerator includes a cheek side plate, a tongue side plate and a supporting plate to form a structure of teeth sleeves, cheek side magnets and tongue side magnets are arranged on the cheek side plate and the tongue side plate respectively, the cheek side magnets and the tongue side magnets form a micro magnetic field environment around roots of to-be-moved teeth receiving orthodontic treatment, physiological magnetic field loss caused by traction of the orthodontic accessory is effectively compensated, metabolism and reconstruction of periodontal tissue of the to-be-moved teeth are promoted, and the orthodontic teeth moving process is accelerated.

3 Claims, 7 Drawing Sheets

(56) References Cited

U.S. PATENT DOCUMENTS

| | | | |
|---|---|---|---|
| 9,775,687 B1* | 10/2017 | Hoyberg | A61C 7/08 |
| 9,839,500 B2* | 12/2017 | Flyash | A61C 19/066 |
| 11,337,780 B1 | 5/2022 | Moon et al. | |
| 2010/0183997 A1* | 7/2010 | Darendeliler | A61C 7/08 |
| | | | 433/24 |
| 2018/0071054 A1* | 3/2018 | Ha | A61C 7/006 |
| 2020/0121420 A1* | 4/2020 | Scurtescu | A61C 7/08 |
| 2022/0361984 A1* | 11/2022 | Philip | A61C 5/30 |
| 2024/0058098 A1* | 2/2024 | Chen | A61N 2/002 |

FOREIGN PATENT DOCUMENTS

| | | |
|---|---|---|
| CN | 115281859 | 11/2022 |
| KR | 20100007710 | 7/2010 |
| WO | 2011055968 | 5/2011 |
| WO | 2021251068 | 12/2021 |

* cited by examiner

MAGNETIC-FIELD-ADJUSTABLE MICROMAGNETIC ORTHODONTIC ACCELERATOR

CROSS-REFERENCE TO RELATED APPLICATION

The disclosure claims priority from Chinese patent application No. 202210986748.8, filed on Aug. 17, 2022, titled with "magnetic-field-adjustable micromagnetic orthodontic accelerator", which is hereby incorporated herein by reference in its entirety for all purposes.

TECHNICAL FIELD

The disclosure relates to the technical field of medical devices, and in particular to a magnetic-field-adjustable micromagnetic orthodontic accelerator.

DESCRIPTION OF RELATED ART

Oral and maxillofacial deformity is one of three major oral diseases in China, with a prevalence rate of 29.3%. Oral and maxillofacial deformities not only affect the beauty of the face, but also may further cause oral diseases, and serious cases may cause psychological barriers, so there is a huge social demand for its prevention and treatment. At present, orthodontic treatment is the most important prevention and treatment method for oral and maxillofacial deformities. The length of orthodontic treatment cycle is affected by patients and treatment-related factors, such as the severity of oral and maxillofacial deformities, patient compliance and the design of treatment programs. Usually, the comprehensive treatment course of orthodontic patients is 12-36 months, but the longer treatment process will increase the risk of enamel demineralization, dental caries, root resorption, bone cracking, bone fenestration and other complications, seriously affecting the quality of life of patients, increasing the cost of treatment, and reducing patient compliance.

Therefore, how to accelerate tooth movement more safely and effectively and shorten the course of orthodontic treatment has become an urgent problem to be solved in the field of orthodontics.

SUMMARY OF THE DISCLOSURE

An embodiment of the disclosure provides a magnetic-field-adjustable micromagnetic orthodontic accelerator, which solves the problems that the existing orthodontic treatment cycle is long and patients are prone to complications.

An embodiment of the disclosure provides a magnetic-field-adjustable micromagnetic orthodontic accelerator, which includes: a cheek side plate and a tongue side plate which are oppositely arranged, where at least one cheek side magnet and at least one tongue side magnet are respectively arranged in the cheek side plate and the tongue side plate, and the at least one cheek side magnet and the at least one tongue side magnet are oppositely arranged in a one-to-one correspondence manner to form at least one pair; a supporting plate configured to connect the cheek side plate and the tongue side plate, an accommodating space is defined among the supporting plate, the cheek side plate and the tongue side plate, so that the magnetic-field-adjustable micromagnetic orthodontic accelerator forms a structure of teeth sleeves; when the magnetic-field-adjustable micromagnetic orthodontic accelerator is used, teeth are placed in the accommodating space, the cheek side plate and the tongue side plate are respectively located at a cheek side and a tongue side of the teeth in the accommodating space, and the cheek side magnet and the tongue side magnet are correspondingly arranged with the root of the teeth, and a micromagnetic field is formed between the paired cheek side magnet and the tongue side magnet to act on the root of the teeth.

BRIEF DESCRIPTION OF THE DRAWINGS

In order to explain the technical solution of embodiments of the disclosure more clearly, the following will briefly introduce the drawings needed to be used in the embodiments. It should be understood that the following drawings only show some embodiments of the disclosure, and therefore should not be regarded as limiting the scope of the disclosure.

REFERENCE NUMERALS

10—magnetic-field-adjustable micromagnetic orthodontic accelerator; 11—cheek side plate; 111—upper cheek side plate; 112—lower cheek side plate; 1—cheek side magnet; 12—tongue side plate; 121—upper tongue side plate; 122—lower tongue side plate; 2—tongue side magnet; 13—supporting plate; 14—accommodating space; 141—first accommodating space; 142—second accommodating space; 15—anterior teeth area; 16—premolar area; 17—molar area; 20—maxillary teeth; 30—mandibular teeth; 40—groove.

DETAILED DESCRIPTION OF EMBODIMENTS

As used herein:

The term "prepared by" is synonymous with the term "including". The terms "including", "having", "containing" or any other variation thereof as used herein are intended to cover non-exclusive inclusion. For example, compositions, steps, methods, articles or devices containing the listed elements need not be limited to those elements, but can include other elements not explicitly listed or elements inherent in such compositions, steps, methods, articles or devices.

The conjunction "consisting of" excludes any unspecified element, step or component. If used in the claim, this phrase will make the claim closed, so that it does not contain materials other than those described, except for conventional impurities related thereto. When the phrase "consisting of" appears in the clause of the subject of the claim rather than immediately following the subject matter, it is limited to the elements described in the clause; Other elements are not excluded from the claims as a whole.

When equivalents, concentrations, or other values or parameters are expressed in terms of ranges, preferred ranges, or ranges defined by a series of upper and lower preferred values, it should be understood that all ranges formed by any pairing of any upper range or preferred value with any lower range or preferred value are specifically disclosed, regardless of whether the range is separately disclosed. For example, when the scope "1-5" is disclosed, the described scope should be interpreted as including the scope "1-4", "1-3", "1-2", "1-2 and 4-5", "1-3 and 5", etc. When a numerical range is described herein, unless otherwise specified, the range is intended to include its end value and all integers and fractions within the range.

In these embodiments, the parts and percentages are calculated by mass unless otherwise specified.

The term "part by mass" refers to the basic unit of measurement that represents the mass ratio of multiple components. One part can represent any unit mass, such as 1 g or 2.689 g, etc. If we say that the part by mass of component A is a and the part by mass of component B is b, it means that a mass ratio of the component A to the component B is a:b. Or, it means that the mass of the component A is aK, and the mass of the component B is bK (K is an arbitrary number, representing multiple factor). Undeniably, unlike mass fractions, the sum of parts by mass of all components is not limited to 100 parts.

The term "and/or" is used to indicate that one or both of the described situations may occur, for example, A and/or B include (A and B) and (A or B).

An embodiment of the disclosure provides a magnetic-filed-adjustable micromagnetic orthodontic accelerator 10, which is used to accelerate the movement of teeth in the orthodontic process, so as to shorten the period of orthodontics. Referring to FIGS. 1 to 4, the magnetic-filed-adjustable micromagnetic orthodontic accelerator 10 includes a cheek side plate 11 and a tongue side plate 12 which are opposite to each other, and a supporting plate 13 for connecting the cheek side plate 11 and the tongue side plate 12.

An accommodating space 14 is defined among the supporting plate 13, the cheek side plate 11 and the tongue side plate 12, and the magnetic-field-adjustable micromagnetic orthodontic accelerator 10 is in a tooth sleeve structure (i.e., structure of teeth sleeves). It can be understood that in order to make the magnetic-field-adjustable micromagnetic orthodontic accelerator 10 take the shape of the teeth sleeves, the supporting plate 13, the cheek side plate 11 and the tongue side plate 12 must be arcs matching the shape of human teeth.

The cheek side plate 11 is a baffle facing the cheek, that is, facing lips when the magnetic-field-adjustable micromagnetic orthodontic accelerator 10 is used, the tongue side plate 12 is a baffle facing the tongue, that is, facing the palate when the magnetic-field-adjustable micromagnetic orthodontic accelerator 10 is used, and the supporting plate 13 is a base plate used to support the teeth.

The cheek side plate 11 and the tongue side plate 12 are respectively provided with at least one cheek side magnet 1 and at least one tongue side magnet 2, and the at least one cheek side magnet 1 and the at least one tongue side magnet 2 oppositely arranged in a one-to-one correspondence manner to form at least one pair. The cheek side magnet 1 and the tongue side magnet 2 can be respectively fixed and arranged in the cheek side plate 11 and the tongue side plate 12. For example, the magnets can be integrally welded and fixed in the teeth sleeves during the preparation of the teeth sleeves. The cheek side magnet 1 and the tongue side magnet 2 can also be detachably arranged on the cheek side plate 11 and the tongue side plate 12 respectively, for example, the magnets can be arranged on the teeth sleeve structure after the teeth sleeve structure is prepared.

The cheek side magnet 1 and the tongue side magnet 2 are arranged in pairs, for example, a pair of the cheek side magnet 1 and the tongue side magnet 2 can be used, that is, one cheek side magnet 1 corresponds to one tongue side magnet 2, the cheek side magnets 1 and the tongue side magnets 2 can also be any number of pairs, including two pairs, three pairs, four pairs, five pairs, six pairs and seven pairs. Just ensure that one cheek side magnet 1 corresponds to one tongue side magnet 2. The number of the cheek side magnets and the tongue side magnets depends on the number of orthodontic teeth, that is, the number of teeth that need to be accelerated. When the magnetic-field-adjustable micromagnetic orthodontic accelerator 10 is used, the teeth are placed in the accommodating space 14, the cheek side plate 11 and the tongue side plate 12 are respectively located at the cheek side and tongue side of the teeth in the accommodating space 14, and the cheek side magnet 1 and the tongue side magnet 2 are correspondingly arranged with the root of the teeth, a micro magnetic field can be formed between the paired cheek side magnet 1 and the tongue side magnet 2 to act on the root of the teeth.

Because of widespread existence of micromagnetic fields in various tissues and organs of the human body, it is of great significance for the maintenance of normal physiological functions of the body, especially for tissue repair and regeneration. During orthodontic treatment, the application of the orthodontic force will destroy the local normal magnetic field microenvironment of periodontal tissue, and affect the metabolism and reconstruction of tissue.

The magnetic-field-adjustable micromagnetic orthodontic accelerator 10 provided by the embodiment of the disclosure forms the micromagnetic environment around the root of the teeth to be moved under orthodontic treatment, effectively compensates the loss of the physiological magnetic field caused by the teeth being pulled by the orthodontic accessories, thereby promoting the metabolism and reconstruction of the periodontal tissue of the teeth to be moved, and speeding up the orthodontic tooth movement process.

The magnetic-field-adjustable micromagnetic orthodontic accelerator 10 has obvious effect of accelerating tooth movement, strong controllability and small side effects. Since the magnetic-field-adjustable micromagnetic orthodontic accelerator 10 specifically acts on the root of the teeth, it will not affect other bone and muscle tissues, thus reducing side effects; The micromagnetic field is induced by the magnet, the intensity of the magnetic field is close to the intensity of the physiological magnetic field. Compared with the electromagnetic pulse, it is more gentle, the intensity is easier to control, and has less side effects on the human body.

In order to ensure that the micromagnetic field formed between the cheek side magnet 1 and the tongue side magnet 2 acts on the root of the teeth, the height of the cheek side plate 11 and the tongue side plate 12 should meet the requirements of covering the groove bone of the root of the teeth. The installation position of the cheek side magnet 1 and the tongue side magnet 2 corresponds to the position from the root to the ⅓ of the neck of the teeth. Because the structure that affects teeth movement is mainly alveolar bone, the height of the cheek side plate 11 and the tongue side plate 12 covers the alveolar bone at the root of the teeth, which can ensure that the micromagnetic field generated between the cheek side magnet 1 and the tongue side magnet 2 acts on the alveolar bone, making the acceleration effect better.

It can be understood that the magnetic-field-adjustable micromagnetic orthodontic accelerator 10 can only be used to accelerate the movement of maxillary teeth or mandibular teeth, that is, only one accommodating space 14 is formed among the supporting plate 13, the cheek side plate 11 and the tongue side plate 12 to accommodate the maxillary teeth or mandibular teeth, and two accommodating spaces 14 can also formed among the supporting plate 13, the cheek side plate 11 and the tongue side plate 12 to accelerate the movement of the maxillary teeth and the mandibular teeth at the same time.

Figure 1:
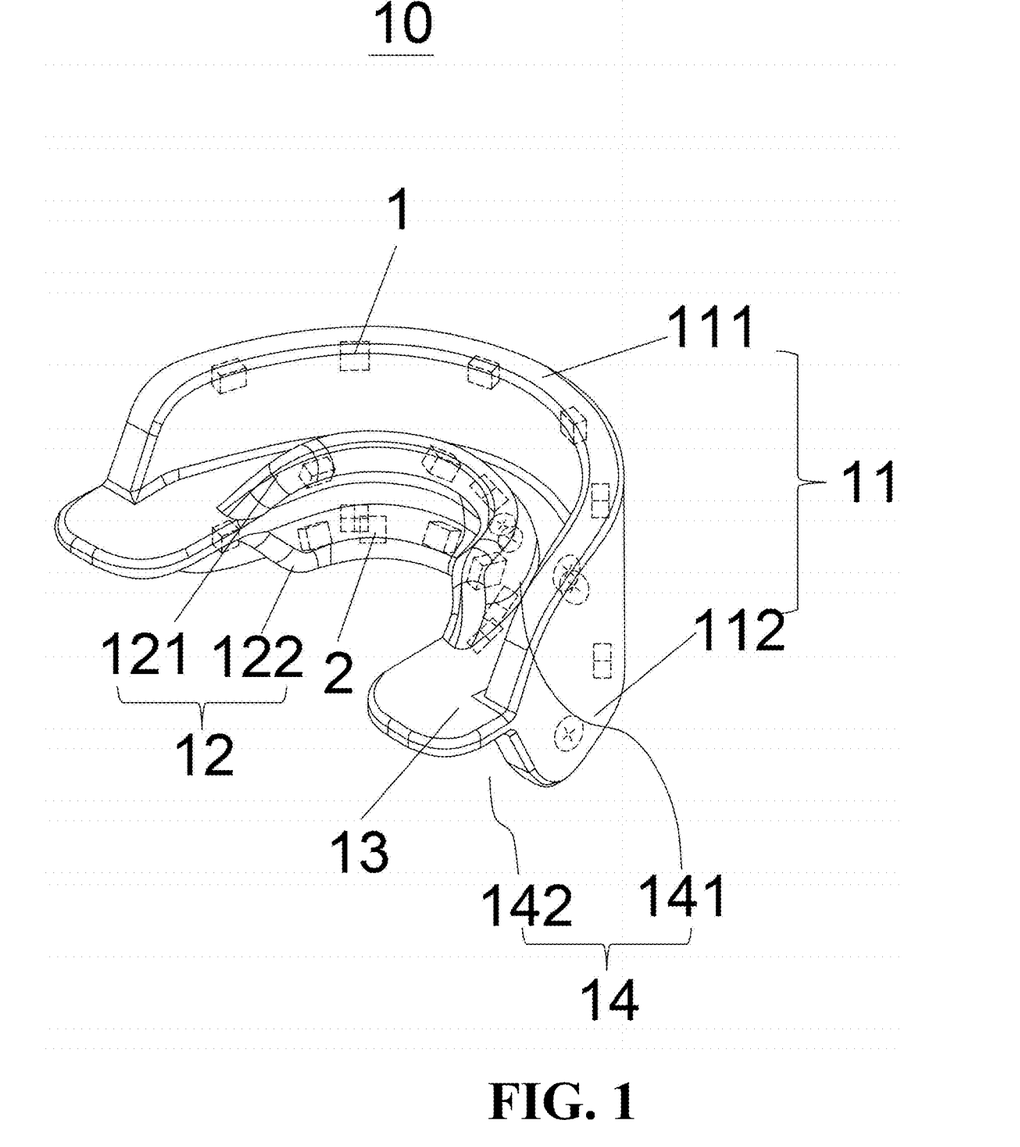
FIG. 1 is a schematic diagram of a three-dimensional (3D) structure of a magnetic-field-adjustable micromagnetic orthodontic accelerator according to an embodiment of the disclosure.
Figure 2:
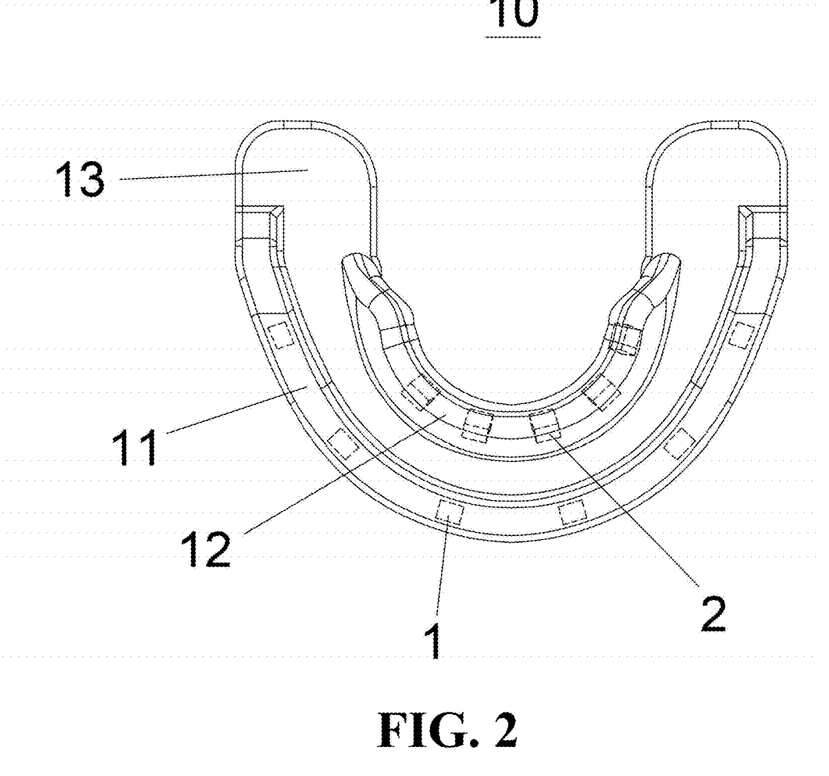
FIG. 2 is a top view of the magnetic-field-adjustable micromagnetic orthodontic accelerator according to the embodiment of the disclosure.
Figure 3:
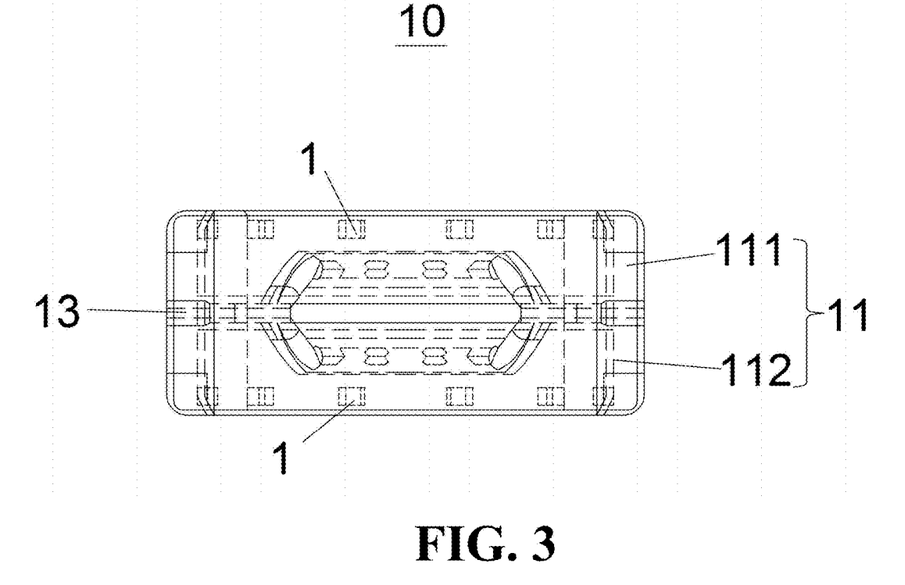
FIG. 3 is a rear view of the magnetic-field-adjustable micromagnetic orthodontic accelerator according to the embodiment of the disclosure.
Figure 4:
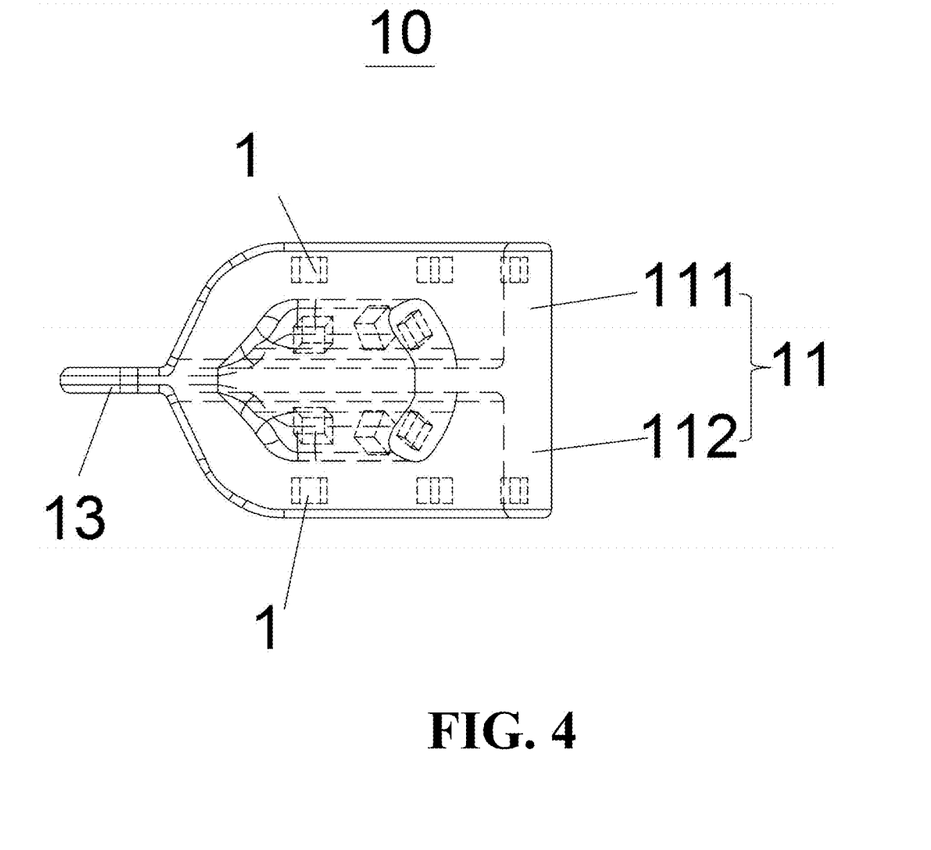
FIG. 4 is a side view of the magnetic-field-adjustable micromagnetic orthodontic accelerator according to the embodiment of the disclosure.
Figure 7:
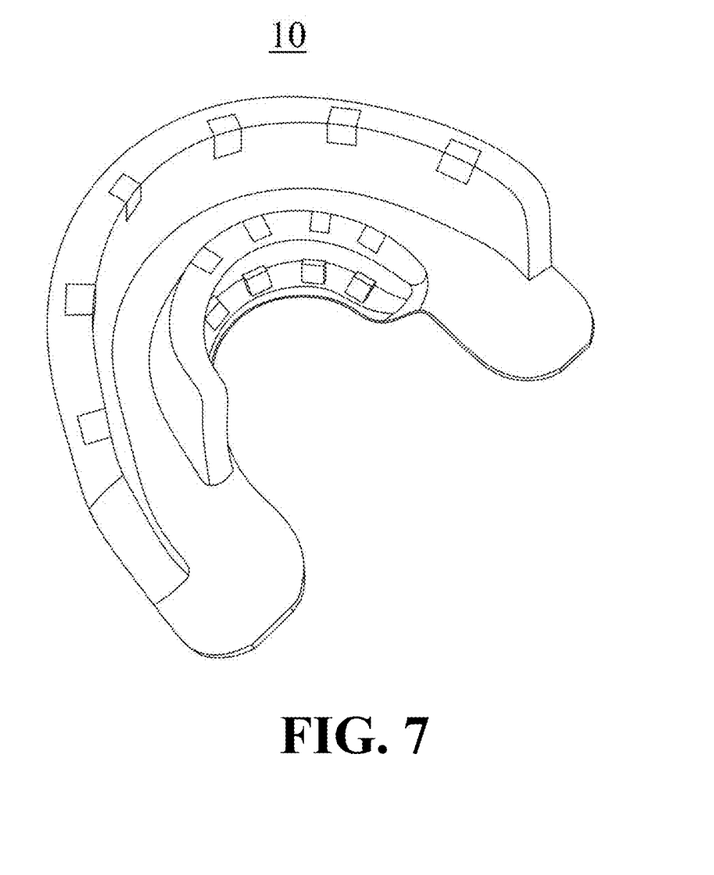
FIG. 7 is a 3D physical view of a magnetic-field-adjustable micromagnetic orthodontic accelerator according to an embodiment of the disclosure.

In an embodiment, referring to FIG. 1 and FIG. 7, the cheek side plate 11 includes an upper cheek side plate 111 and a lower cheek side plate 112 symmetrically arranged relative to the supporting plate 13. The tongue side plate 12 includes an upper tongue side plate 121 and a lower tongue side plate 122 symmetrically arranged relative to the supporting plate 13, the accommodating space 14 includes a first accommodating space 141 and a second accommodating space 142 symmetrically arranged up and down, the upper tongue side plate 111, the upper tongue side plate 121 and the supporting plate 13 define the first accommodating space 141, and the lower cheek side plate 112, the lower tongue side plate 122 and the supporting plate 13 define the second accommodating space 142, the first accommodating space 141 is used to place the maxillary teeth 20, and the second accommodating space 142 is used to place the mandibular teeth 30, so that the maxillary teeth 20 and the mandibular teeth 30 can be accelerated to move at the same time.

The up and down directions of the magnetic-field-adjustable micromagnetic orthodontic accelerator 10 are perpendicular to the supporting plate 13. Because the magnetic-field-adjustable micromagnetic orthodontic accelerator 10 is symmetrically arranged up and down with the supporting plate 13 as the axis of symmetry, the up and down directions of the magnetic-field-adjustable micromagnetic orthodontic accelerator 10 can be changed at will.

The cheek side magnets 1 are arranged in the upper cheek side plate 111 and the lower cheek side plate 112, and the tongue side magnets 2 are arranged in the upper tongue side plate 121 and the lower tongue side plate 122, so as to form the micro magnetic fields between the maxillary teeth 20 and the mandibular teeth 30.

In some embodiments, the intensity of the micromagnetic field is 10~30 millitesla (mT), for example, it can be 10~15 mT, or 15~20 mT, or 20~25 mT, and more specifically, it can be 10 mT, 11 mT, 12 mT, 13 mT, 14 mT, 15 mT, 16 mT, 17 mT, 18 mT, 19 mT, 20 mT, 21 mT, 22 mT, 23 mT, 24 mT, 25 mT, 26 mT, 27 mT, 28 mT, 29 mT, or 30 mT. The intensity range of the magnetic field is close to the physiological magnetic field intensity, with small side effects. In some embodiments, the intensity of the micromagnetic field is 10-20 mT. Referring to FIGS. 1 and 7, each of the cheek side plate 11 and the tongue side plate 12 includes an anterior teeth area 15, a premolar area 16 and a molar area 17. The cheek side magnets 1 and the tongue side magnets 2 are respectively arranged in the anterior teeth areas 15, the premolar areas 16 and the molar areas 17 of the cheek side plate 11 and the tongue side plate 12.

The anterior teeth areas 15 of the cheek side plate 11 and the tongue side plate 12 correspond to the anterior teeth of the maxillary teeth 20 and the mandibular teeth 30 respectively, the premolar areas 16 of the cheek side plate 11 and the tongue side plate 12 correspond to the premolars of the maxillary teeth 20 and the mandibular teeth 30 respectively, and the molar areas 17 of the cheek side plate 11 and the tongue side plate 12 correspond to the molars of the maxillary teeth 20 and the mandibular teeth 30 respectively. The cheek side magnets 1 and the tongue side magnets 2 are relatively arranged on the anterior teeth areas, the premolar areas and the molar areas, which can accelerate the movement of all teeth, and are suitable for patients with orthodontics.

In some embodiments, the number of the cheek side magnets 1 and the tongue side magnets 2 is 2 to 12, and the number of the cheek side magnets 1 and the tongue side magnets 2 is the same, which are 2 to 12, respectively, for example, 2, 3, 4, 5, 6, 7, 8, 9, 10, 11 or 12.

In a preferred embodiment, the intensity of the micromagnetic field formed in the anterior teeth area 15 is 20-25 mT, the intensity of the micromagnetic field formed in the premolar area 16 is 15-20 mT, and the intensity of the micromagnetic field formed in the molar area 17 is 10-15 mT. The micromagnetic field intensity required by teeth in different tooth positions is different, so it can meet the personalized requirements of teeth in different areas for magnetic field during orthodontic treatment.

In some embodiments, among the paired cheek side magnet 1 and the tongue side magnet 2, in the connecting direction of the cheek side magnet 1 and the tongue side magnet 2, the magnetic pole directions of the cheek side magnet 1 and the tongue side magnet 2 are set along the same direction.

Specifically, the connecting direction of each pair of cheek side magnets 1 and tongue side magnets 2 runs through the teeth, and the micromagnetic field formed between each pair of cheek side magnets 1 and tongue side magnets 2 acts on the root of the teeth between them. In order to better form the micromagnetic field between the cheek side magnet 1 and the tongue side magnet 2, the magnetic poles of the cheek side magnet 1 and the tongue side magnet 2 in the direction running through the teeth are the same. Since all magnets have N poles and S poles, the magnetic field direction between the magnets goes from N pole to S pole, so the magnetic pole direction between each pair of cheek side magnets 1 and tongue side magnets 2 is the same, which can ensure that the magnets located on both sides of the teeth in the accommodating space 14 can better form micromagnetic fields to act on the teeth.

For example, the cheek side magnet 1 is S-pole in the direction close to the teeth and N-pole in the direction far away from the teeth, then the tongue side magnet 2 is N-pole in the direction close to the teeth and S-pole in the direction far away from the teeth, so that in the connecting direction between the cheek side magnet 1 and the tongue side magnet 2, the magnetic poles of the cheek side magnet 1 and the tongue side magnet 2 are the same, and the micromagnetic field direction is that the N-pole of the tongue side magnet 2 faces the S-pole of the cheek side magnet 1, acting on the teeth.

In other embodiments, the cheek side magnet 1 may be N-pole in the direction close to the teeth and S-pole in the direction far away from the teeth, so that the tongue side magnet 2 is S-pole in the direction close to the teeth and N-pole in the direction far away from the teeth.

On the basis of any of the above embodiments, optionally, the cheek side magnet 1 is detachably arranged on the cheek side plate 11, and the tongue side magnet 2 is detachably arranged on the tongue side plate 12. The cheek side magnet 1 and the tongue side magnet 2 are detachably arranged, so that the magnetic-field-adjustable micromagnetic orthodontic accelerator 10 can change and set micromagnets with different intensities according to different treatment stages, different teeth and different patients' different requirements for magnetic fields in orthodontic treatment. According to the magnetic fields required by different patients and different tooth positions in different treatment stages, the corresponding micromagnets are installed in the corresponding teeth positions to realize the construction of personalized micromagnetic environment, so as to meet the individualized requirements of different opportunities and areas for magnetic fields during orthodontic treatment.

The intensity of the micromagnets of the magnetic-field-adjustable micromagnetic orthodontic accelerator 10 can be flexibly adjusted. The magnetic fields generated by the micromagnets in different areas correspond to different teeth positions, and their action range matches the anatomical morphology of the dentition of Asian people. Micromagnets with different magnetic field intensities can be used in different orthodontic treatment periods and different tooth positions, which can more pertinently meet the individualized clinical needs of different patients, efficiently regulate and control the periodontal tissue reconstruction activities of orthodontic teeth, increase the moving speed of orthodontic teeth, reduce side effects, and realize accurate individualized orthodontic accelerated treatment.

Figure 5:
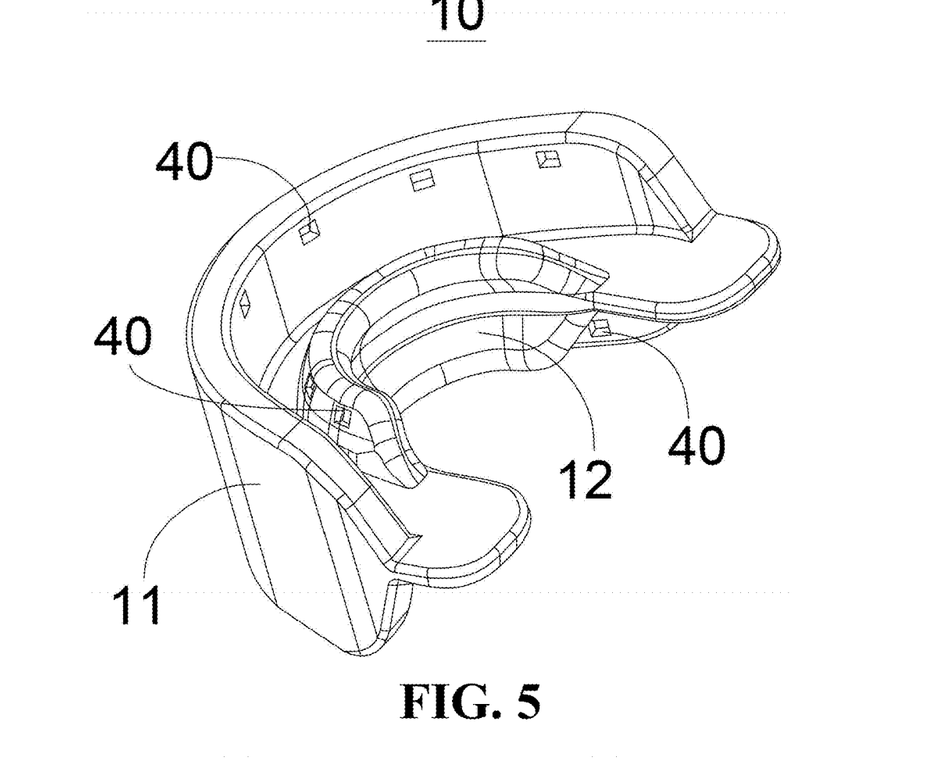
FIG. 5 is a schematic diagram of a 3D structure of a magnetic-field-adjustable micromagnetic orthodontic accelerator according to another embodiment of the disclosure.
Figure 6:
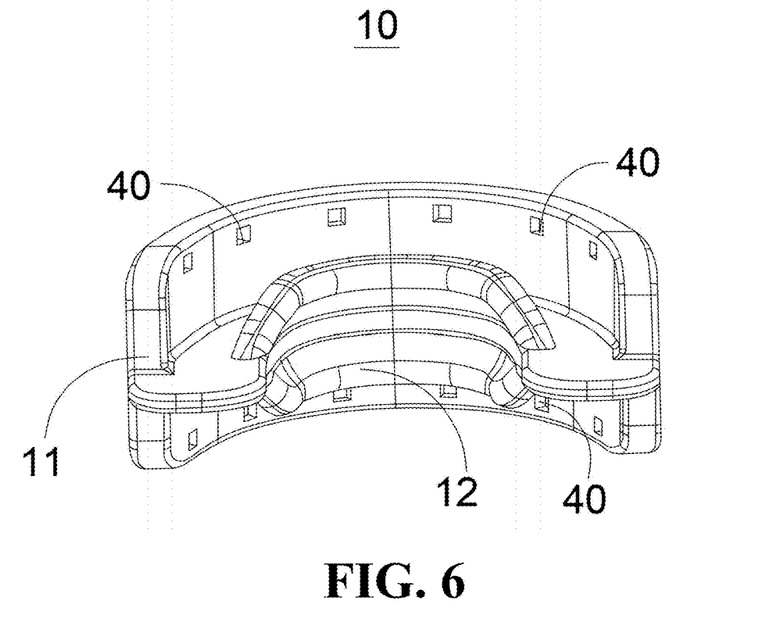
FIG. 6 is a front view of a magnetic-field-adjustable micromagnetic orthodontic accelerator according to another embodiment of the disclosure.

In an alternative embodiment, please refer to FIGS. 5 and 6, the cheek side plate 11 and the tongue side plate 12 are respectively provided with grooves 40, and each groove 40 is in a convergent shape, that is, the width of the opening of the groove 40 is smaller than that of the inner space, and the cheek side magnet 1 and the tongue side magnet 2 are inserted into the cheek side plate 11 and the tongue side plate 12 through the grooves 40, respectively. The opening edges of the grooves 40 form lock latches for the cheek side magnets 1 and the tongue side magnets 2. The cheek side plate 11 and the tongue side plate 12 are made of elastic materials, and the opening of the groove 40 is smaller than that of the inner space. The cheek side magnet 1 and the tongue side magnet 2 can be inserted into the grooves 40 by the elasticity of the opening of the grooves 40. After the cheek side magnet 1 and the tongue side magnet 2 enter the grooves 40 respectively, the opening of the grooves 40 are restored to their original states. Because the opening is small, the cheek side magnet 1 and the tongue side magnet 2 can be locked, and the cheek side magnet 1 and the tongue side magnet 2 will not fall off, thus causing no risk of aspiration to patients.

Figure 8:
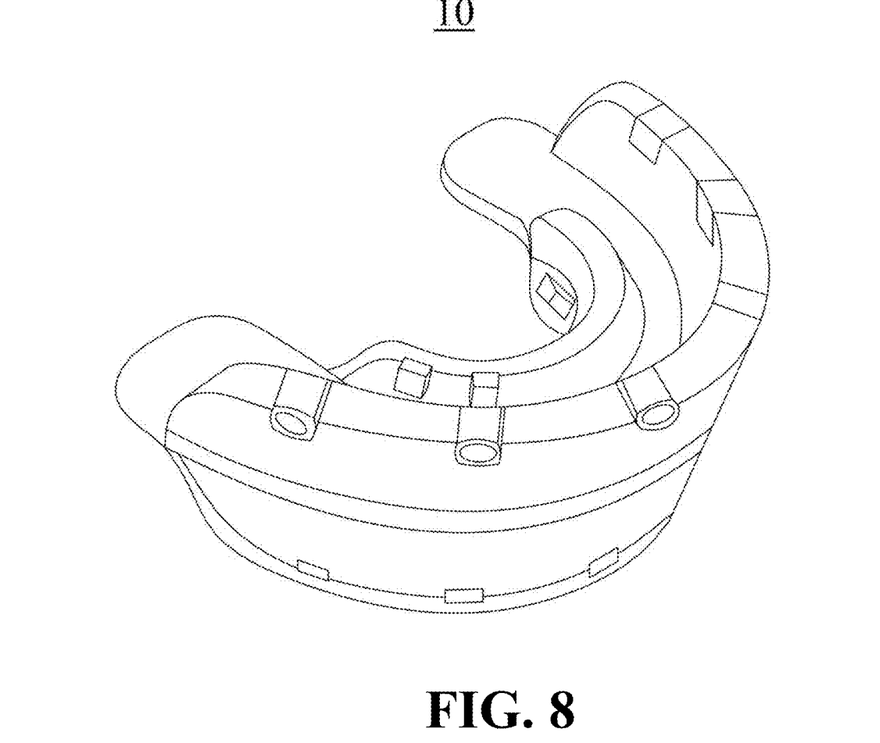
FIG. 8 is another 3D physical diagram of the magnetic-field-adjustable micromagnetic orthodontic accelerator according to the embodiment of the disclosure.

In some embodiments, the supporting plate 13, the cheek side plate 11 and the tongue side plate 12 are made of a silicone material, the silicone material includes soft silicone or hard silicone, the soft silicone has the advantages of high elasticity and plasticity, and the hard silicone has the advantages of high hardness and strong fatigue resistance, as shown in FIG. 7 and FIG. 8, FIGS. 7 and 8 are physical pictures of the magnetic-field-adjustable micromagnetic orthodontic accelerator 10 of the disclosure, a transparent tooth-like magnetic-field-adjustable micromagnetic orthodontic accelerator 10 is made of the silicone material.

The silicone has good biocompatibility, no irritation, no toxicity, no allergic reaction to human tissues, and few rejection reactions; The silicone has good physical and chemical properties, and it can keep its original elasticity and softness in contact with body fluids and tissues without being degraded. It is a fairly stable inert substance. It has high temperature resistance and disinfection. The silicone is easy to process and shape, easy to process and carve, and easy to use. The silicone is wear-resistant, waterproof and long in service life.

Using the silicone material, after the patient bites the supporting plate 13, the magnetic-field-adjustable micromagnetic orthodontic accelerator 10 will not cause occlusal burden to the patient, and the accelerator surface is smooth and round, which will not scratch the oral mucosa. It has good comfort and safety when worn. The micromagnets can be stably arranged in the orthodontic accelerator, and the micromagnets will not come out in the process of taking off the orthodontic accelerator, thus causing no risk of aspiration to patients. The orthodontic accelerator is small in size and has a box-shaped power supply without mouth, which makes it easier to wear and carry around, and does not affect the daily life of patients.

The embodiments of the disclosure will be described in detail below with reference to specific examples, but those skilled in the art will understand that the following examples are only used to illustrate the disclosure, and should not be regarded as limiting the scope of the disclosure. If the specific conditions are not indicated in the examples, the conventional conditions or the conditions suggested by the manufacturer shall be followed. The reagents or instruments used, if the manufacturer is not indicated, are conventional products that can be purchased on the market.

Figure 9:
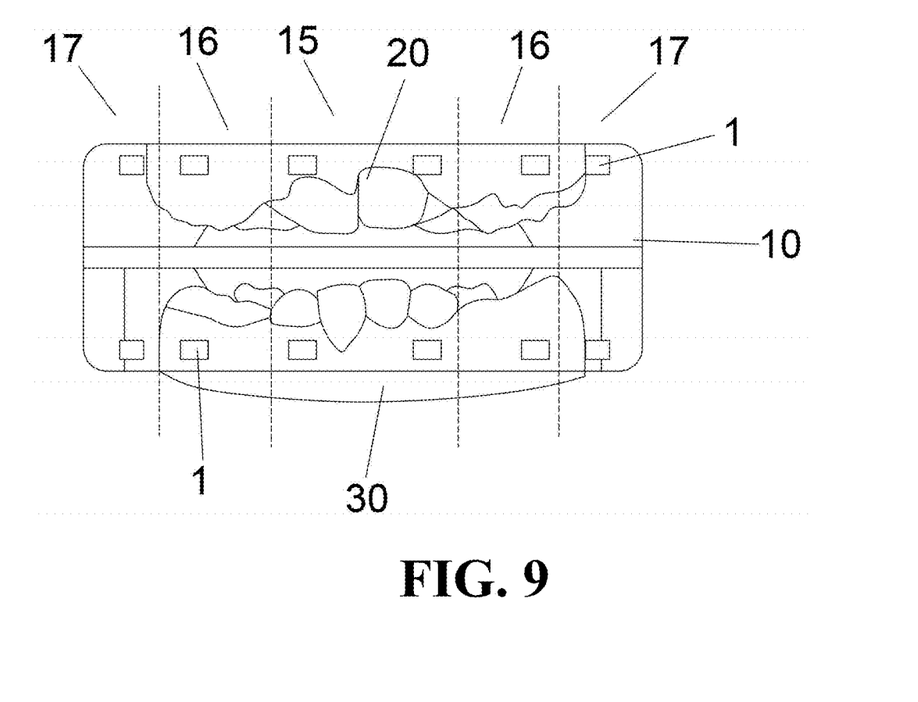
FIG. 9 is a schematic diagram of a magnetic-field-adjustable micromagnetic orthodontic accelerator when in use according to an embodiment of the disclosure.
Figure 10:
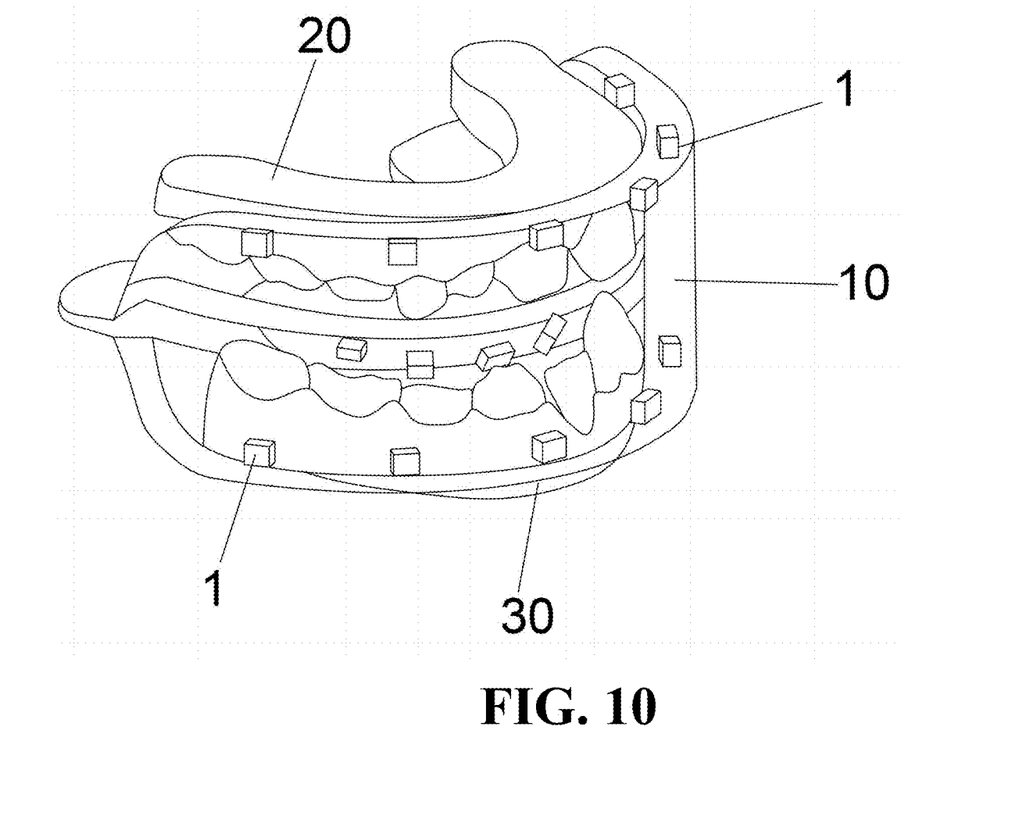
FIG. 10 is another schematic diagram of a magnetic-field-adjustable micromagnetic orthodontic accelerator when in use according to an embodiment of the disclosure.

Example 1: Detection of the magnetic field distribution of a magnetic-field-adjustable micromagnetic orthodontic accelerator is as shown in FIGS. 9 and 10, the micromagnets of grade I, II and III are placed into the micromagnet grooves of the anterior tooth areas 15, the premolar areas 16 and the molar area s17 of the cheek side plate 11 and the tongue side plate 12, and the above-mentioned magnetic-field-adjustable micromagnetic orthodontic accelerator 10 is placed on the horizontal plane, the three-dimensional magnetic field distribution of the magnetic-field-adjustable micromagnetic orthodontic accelerator was measured by a high-precision industrial Gauss meter driven by an external motor. A magnetic field of about 20-25 mT was formed in the root of the anterior teeth areas, a magnetic field of about 15-20 mT was formed in the root of the premolar areas, and a magnetic field of about 10-15 mT was formed in the root of the molar areas.

Through the magnetic field intensity test, it can be seen that the micromagnetic field intensity generated by this magnetic-field-adjustable micromagnetic orthodontic accelerator is about 10 mT-30 mT, which accords with the physiological magnitude. No matter in the horizontal or vertical direction, the magnetic field is mainly distributed in the root area, and the magnetic field intensity in other areas is low, which can effectively concentrate the micromagnetic effect on the teeth and alveolar bones that need to be accelerated.

Compared with the prior art, the beneficial effects of this disclosure include:

The magnetic-field-adjustable micromagnetic orthodontic accelerator provided by the embodiment of the disclosure forms a micro-magnetic field environment around the root of the teeth to be moved undergoing orthodontic treatment, effectively compensating the loss of physiological magnetic field caused by the teeth being pulled by orthodontic accessories, further promoting the metabolism and reconstruction of periodontal tissues of the tooth to be moved, and accelerating the orthodontic tooth movement process.

The intensity of the micromagnets of the magnetic-field-adjustable micromagnetic orthodontic accelerator can be flexibly adjusted. The magnetic fields generated by the micro-magnets in different areas correspond to different teeth positions, and their range of action is matched with the anatomical morphology of dentition of Asian people. Micromagnets with different magnetic field intensities can be used in different orthodontic treatment periods and different teeth positions, which can more pertinently meet the individualized clinical needs of different patients, efficiently regulate and control the periodontal tissue reconstruction activities of orthodontic teeth, increase the moving speed of orthodontic teeth, reduce side effects, and realize accurate individualized orthodontic accelerated treatment.

Using the silicone material, after the patient bites the supporting plate, the magnetic-field-adjustable micromagnetic orthodontic accelerator will not cause occlusion burden to the patient, and the accelerator surface is smooth and round, which will not scratch the oral mucosa. It has good comfort and safety when worn. The micromagnet can be stably arranged in the magnetic-field-adjustable micromagnetic orthodontic accelerator, and the micromagnet will not come out in the process of taking off the magnetic-field-adjustable micromagnetic orthodontic accelerator, thus causing no risk of aspiration to patients. The size of the magnetic-field-adjustable micromagnetic orthodontic accelerator is small, and it has a box-type power supply without mouth, which is more convenient to wear and carry, and does not affect the daily life of patients. Moreover, the material used in the magnetic-field-adjustable micromagnetic orthodontic accelerator is odorless and non-toxic, with stable chemical and physical properties, wear resistance, good water resistance and long service life.

Finally, it should be noted that the above embodiments are only used to illustrate the technical solutions of the disclosure, not to limit it; Although the disclosure has been described in detail with reference to the preceding embodiments, those skilled in the art should understand that they can still modify the technical solutions recorded in the preceding embodiments, or replace some or all of the technical features equally; These modifications or substitutions do not make the essence of the corresponding technical solutions separate from the scope of the technical solutions of the embodiments of the disclosure. In addition, those skilled in the art can understand that although some embodiments herein include some features included in other embodiments rather than other features, the combination of features of different embodiments means that they are within the scope of the disclosure and form different embodiments.

For example, in the above claims, any one of the claimed embodiments can be used in any combination. The information disclosed in the background technology part is only intended to deepen the understanding of the overall background technology of this disclosure, and should not be considered as recognition or implied in any form that the information constitutes a prior art that has been known to those skilled in the art.

What is claimed is:

1. A magnetic field adjustable micro-magnetic orthodontic accelerator, comprising:

a buccal side plate and a lingual side plate arranged opposite to each other, with buccal side magnets installed in the buccal side plate and lingual side magnets installed in the lingual side plate, wherein the buccal side magnets and the lingual side magnets are positioned opposite to each other in pair, and at least three pair of the buccal side magnets and the lingual side magnets are provided; and a support plate for connecting the buccal side plate and lingual side plate, to form an accommodating space defined by the support plate, the buccal side plate, and the lingual side plate, giving the magnetic field adjustable micro-magnetic orthodontic accelerator a dental brace structure;

wherein when the magnetic field adjustable micro-magnetic orthodontic accelerator is in use, teeth are placed within the accommodating space, with the buccal side plate and lingual side plate separately positioned on a buccal side and a lingual side of the teeth within the accommodating space, and the buccal side magnets and the lingual side magnets correspondingly positioned to roots of the teeth; and micro-magnetic fields acting on the roots of the teeth are formed between the buccal side magnets and the lingual side magnets in pair;

the buccal side plate and the lingual side plate each comprise an anterior tooth area, a premolar area, and a molar area; the buccal side magnets and the lingual side magnets are arranged opposite to each other in the anterior tooth area, the premolar area, and the molar area;

a number of the buccal side magnets and a number of the lingual side magnets are both 3 to 12;

a micro-magnetic field formed in the anterior tooth area has an intensity of 20-25 mT, a micro-magnetic field formed in the premolar area has an intensity of 15-20 mT, and a micro-magnetic field formed in the molar area has an intensity of 10-15 mT;

the buccal side magnets are detachably installed on the buccal side plate, and the lingual side magnets are detachably installed on the lingual side plate;

the buccal side plate and lingual side plate are provided with tapered grooves; the buccal side magnets and lingual side magnets are inserted into the buccal side plate and the lingual side plate through the tapered grooves, with open edges of the tapered grooves forming locks for the buccal side magnets and lingual side magnets; and the support plate, the buccal side plate, and the lingual side plate are made of a silicone material, and the silicone material comprises soft silicone or hard silicone.

2. The magnetic field adjustable micro-magnetic orthodontic accelerator according to claim 1, wherein the buccal side plate comprises an upper buccal side plate and a lower buccal side plate that are symmetrically arranged with respect to the support plate; the lingual side plate comprises an upper lingual side plate and a lower lingual side plate that are symmetrically arranged with respect to the support plate; the accommodating space comprises a first accommodating space and a second accommodating space arranged in upper and lower positions respectively, with the upper buccal side plate, the upper lingual side plate, and the support plate forming the first accommodating space, and the lower buccal side plate, the lower lingual side plate, and the support plate forming the second accommodating space; the first accommodating space is used for placing maxillary teeth and the second accommodating space is used for placing mandibular teeth.

3. The magnetic field adjustable micro-magnetic orthodontic accelerator according to claim 1, wherein in the buccal side magnets and the lingual side magnets in pair, in a connection direction of each of the buccal side magnets and a corresponding one of the lingual side magnets, magnetic poles of each of the buccal side magnets and the corresponding one of the lingual side magnets are set along a same direction.

* * * * *